US008334406B2

(12) United States Patent
May et al.

(10) Patent No.: US 8,334,406 B2
(45) Date of Patent: Dec. 18, 2012

(54) PROCESS FOR PREPARING CARBOXAMIDES BY HYDROLYSIS CARBOXYLIC ACID NITRILES IN THE PRESENCE OF A CATALYST COMPRISING MANGANESE DIOXIDE

(75) Inventors: Alexander May, Darmstadt (DE); Jochen Ackermann, Muehltal (DE); Hermann Siegert, Seeheim-Jugenheim (DE); Bernd Vogel, Wiesbaden (DE); Soenke Broecker, Ober-Ramstadt (DE)

(73) Assignee: Evonik Roehm GmbH, Darmstadt (DE)

( * ) Notice: Subject to any disclaimer, the term of this patent is extended or adjusted under 35 U.S.C. 154(b) by 559 days.

(21) Appl. No.: 12/515,036

(22) PCT Filed: Aug. 30, 2007

(86) PCT No.: PCT/EP2007/059041
§ 371 (c)(1),
(2), (4) Date: May 15, 2009

(87) PCT Pub. No.: WO2008/061822
PCT Pub. Date: May 29, 2008

(65) Prior Publication Data
US 2011/0060159 A1 Mar. 10, 2011

(30) Foreign Application Priority Data

Nov. 22, 2006 (DE) .................. 10 2006 055 430

(51) Int. Cl.
*C07C 231/00* (2006.01)
*C07C 67/20* (2006.01)
*C07C 67/22* (2006.01)

(52) U.S. Cl. ....................... 564/126; 560/215

(58) Field of Classification Search .............. None
See application file for complete search history.

(56) References Cited

U.S. PATENT DOCUMENTS

| 4,560,508 | A | * | 12/1985 | Matsuo et al. ............... 540/364 |
| 4,987,256 | A | | 1/1991 | Ebata et al. |
| 5,087,750 | A | | 2/1992 | Uda et al. |
| 5,756,842 | A | | 5/1998 | Tanaka et al. |
| 6,075,162 | A | * | 6/2000 | Kida .......................... 560/212 |
| 6,124,501 | A | * | 9/2000 | Sugano et al. ............... 564/126 |
| 6,743,407 | B2 | | 6/2004 | Schaefer et al. |
| 6,977,310 | B2 | | 12/2005 | Ackermann et al. |

(Continued)

FOREIGN PATENT DOCUMENTS

EP 0 379 111 7/1990

(Continued)

OTHER PUBLICATIONS

U.S. Appl. No. 12/298,034, filed Oct. 22, 2008, May, et al.

(Continued)

*Primary Examiner* — Susanna Moore
*Assistant Examiner* — Jennifer C Sawyer
(74) *Attorney, Agent, or Firm* — Oblon, Spivak, McClelland, Maier & Neustadt, L.L.P.

(57) ABSTRACT

The present invention relates to a process for preparing carboxamides by hydrolysing carbonitriles in the presence of a catalyst comprising manganese dioxide, wherein the reaction mixture added to the catalyst comprising manganese dioxide has a pH in the range of 6.0 to 11.0 and the hydrolysis is performed in the presence of an oxidizing agent. The present invention further relates to a process for preparing alkyl (meth)acrylates, the process having a hydrolysis step according to the process described above.

27 Claims, 1 Drawing Sheet

U.S. PATENT DOCUMENTS

| | | |
|---|---|---|
| 6,979,432 B2 | 12/2005 | Schaefer et al. |
| 7,288,402 B2 | 10/2007 | Osswald et al. |
| 7,491,521 B2 | 2/2009 | Osswald et al. |
| 2006/0211880 A1 | 9/2006 | Ackermann et al. |
| 2008/0194862 A1 | 8/2008 | Ackermann et al. |
| 2008/0194875 A1 | 8/2008 | Ackermann et al. |
| 2008/0248538 A1 | 10/2008 | Osswald et al. |
| 2008/0269431 A1 | 10/2008 | Sarcinelli et al. |
| 2009/0118533 A1 | 5/2009 | Broell et al. |
| 2011/0034728 A1 | 2/2011 | May et al. |
| 2011/0306784 A1 | 12/2011 | May et al. |

FOREIGN PATENT DOCUMENTS

| | | |
|---|---|---|
| EP | 0 412 310 | 2/1991 |
| EP | 0 418 512 | 3/1991 |
| EP | 0 433 611 | 6/1991 |
| EP | 0 545 697 | 6/1993 |
| EP | 0 773 212 | 5/1997 |
| EP | 0 941 984 | 9/1999 |
| EP | 0 945 429 | 9/1999 |
| EP | 0 956 898 | 11/1999 |
| JP | 9 104665 | 4/1997 |
| JP | 2623810 | 4/1997 |

OTHER PUBLICATIONS

U.S. Appl. No. 12/307,773, filed Jan. 7, 2009, Ackermann, et al.
U.S. Appl. No. 12/441,145, filed Mar. 13, 2009, May, et al.
U.S. Appl. No. 12/443,784, filed Mar. 31, 2009, Vogel, et al.
U.S. Appl. No. 12/442,415, filed Mar. 23, 2009, Vogel, et al.
U.S. Appl. No. 12/303,161, filed Dec. 2, 2008, Marx, et al.
U.S. Appl. No. 12/300,189, filed Nov. 10, 2008, Broell, et al.
U.S. Appl. No. 12/299,217, filed Oct. 31, 2008, Broell, et al.
Russian Office Action issued Nov. 8, 2011, in Patent Application No. 2009123372.
E.N. Silberman, "Reaction with Hydrogen Peroxide and Water in the Presence of Bases and Other Hydration Reactions", Chapter 4, pp. 74-86 (with Partial English-language translation).
Third Party Observation dated Dec. 28, 2011, in the corresponding European Application No. 07803050.9.

* cited by examiner

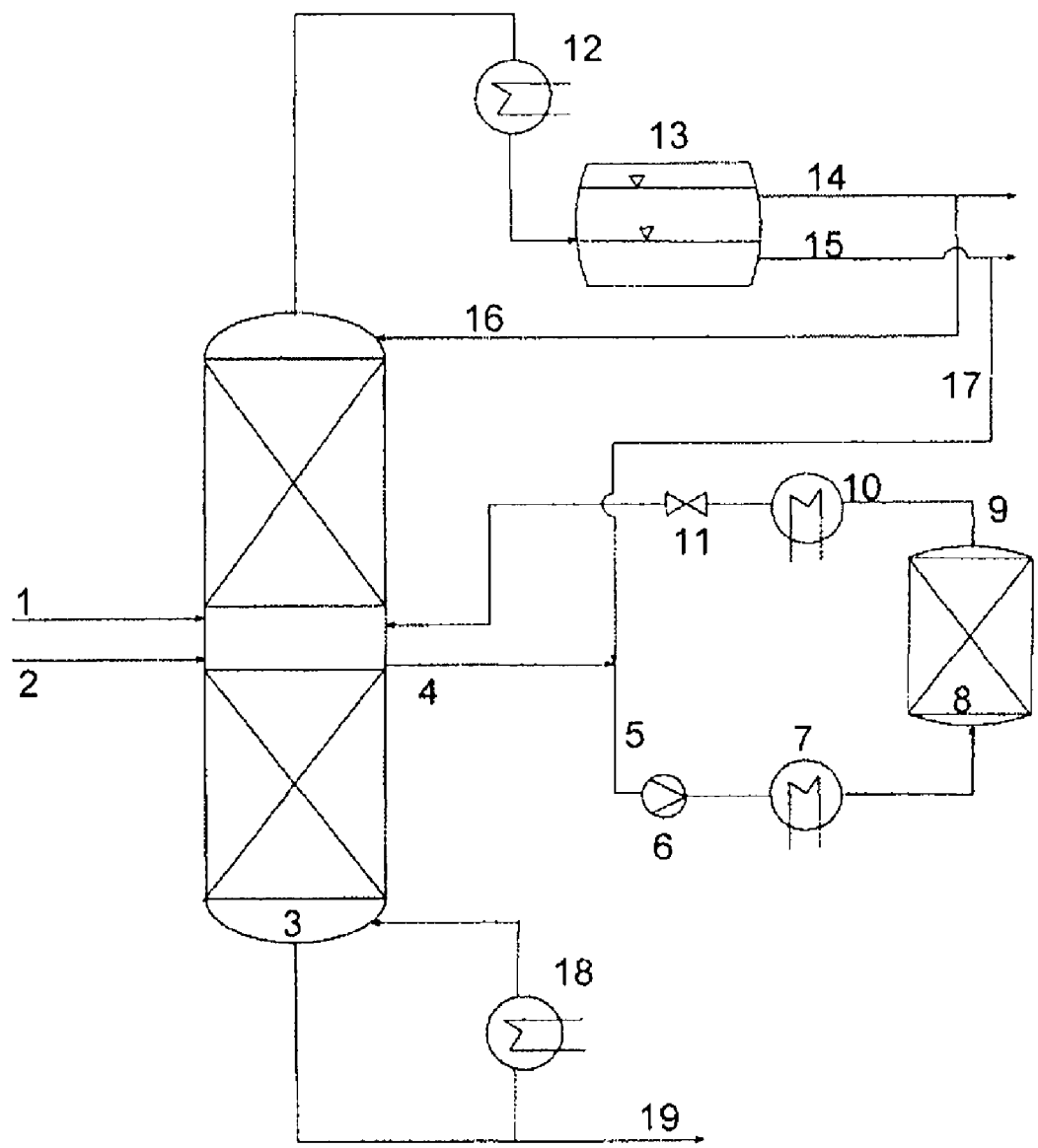

PROCESS FOR PREPARING CARBOXAMIDES BY HYDROLYSIS CARBOXYLIC ACID NITRILES IN THE PRESENCE OF A CATALYST COMPRISING MANGANESE DIOXIDE

CROSS-REFERENCE TO RELATED APPLICATIONS

The present application is a 35 U.S.C. §371 national stage patent application of international patent application PCT/EP2007/059041, filed on Aug. 30, 2007, the text of which is incorporated by reference, and claims the benefit of the filing date of German Patent Application No. 10 2006 055 430.2, filed on Nov. 22, 2006, the text of which is also incorporated by reference.

STATEMENT REGARDING FEDERALLY SPONSORED RESEARCH OR DEVELOPMENT

Not Applicable.

THE NAMES OF THE PARTIES TO A JOINT RESEARCH AGREEMENT

Not Applicable.

INCORPORATION-BY-REFERENCE OF THE MATERIAL ON THE COMPACT DISC

Not Applicable.

BACKGROUND OF THE INVENTION

Field of the Invention

The present invention relates to processes for preparing carboxamides by hydrolysing carbonitriles in the presence of a catalyst comprising manganese dioxide. The present invention further relates to a process for preparing alkyl (meth) acrylates.

The preparation of carboxamides by the hydrolysis of carbonitriles in the presence of a catalyst comprising manganese dioxide is long-established prior art. Carboxamides are in many cases required as an intermediate in industry. For example, α-hydroxyisobutyramide can serve to prepare methacrylic acid or methacrylic esters, especially methyl methacrylate.

Description of the related art including information disclosed under 37 CFR 1.97 and 1.98

By way of example for many documents, reference is made to the publication DE 1593320. DE 1593320 describes a process for hydrolysing nitriles to amides with the aid of manganese dioxide in which yields up to over 90% have been achieved with aliphatic nitriles. This process affords good yields with a high speed. However, a disadvantage is the low service life of the catalyst. In continuous processes, production therefore has to be interrupted after a short time to exchange the catalyst. This operation is associated with very high costs, the productivity of the overall process being lowered by the interruption.

The patent JP 09104665 describes the preparation of active δ-manganese dioxide and defines its activity via the size of the surface area. The catalyst described herein exhibits a very high activity. However, the above-described problem of low service life exists here too. This is especially true of catalysts which have a particularly large surface area.

To improve the lifetime of the catalysts used for the hydrolysis, many efforts have already been undertaken. For example, the document EP 379 111 A2 describes the hydrolysis of α-hydroxycarbonitriles in the presence of manganese dioxide catalysts which have a high content of alkali metals. As a result of this high content of alkali metals, these catalysts exhibit a particularly high activity and service life. The hydrolysis can be performed in particular at a pH in the range of 4 to 8. However, a pH within this range without the use of the catalysts specified in detail in this publication does not lead to a long service life of the catalysts (cf. EP 379 111 A2, Comparative Example 1).

In addition, the publication EP 545 697 A1 presents the use of certain heteropolyacids in order to improve the lifetime of the catalyst. A further improvement in the lifetime of the catalyst can be achieved by the use of promoters. The compounds are added to the system during the reaction. The pH in the hydrolysis reaction should be less than 4, since the acetone cyanohydrin used otherwise lowers the lifetime of the catalyst. At pH values of above 4, the acetone cyanohydrin used can decompose easily to form by-products which impair the catalyst properties. This publication explicitly contradicts the teaching of the document EP 379 111 A2 (cf. EP 545 697 A1, page 3 lines 3 to 6).

In addition, the publication EP 433 611 A1 describes the use of oxidizing agents to stabilize the catalysts. Similarly, the document EP 945 429 A1 describes the use of oxidizing agents for prolonging the catalyst service life, a further improvement being achievable by the addition of small amounts of amines. An adjustment of the pH to a predetermined value is not described in either of the documents EP 433 611 A1 and EP 945 429 A1, and improvement in the service life of catalysts being achievable merely by the use of amines according to document EP 773 212 A1. Therefore, the improvement described in EP 945 429 A1 does not result from an adjustment of the pH, but rather from the combination of the teachings of documents EP 773 212 A1 and EP 433 611 A1. It should be emphasized in this context that cyanohydrins in particular are generally stabilized by addition of acids, so that the experimental data detailed in the examples have probably been obtained under acidic conditions. This is also evident, for example, from the publication EP 379 611 A2 cited above. Therefore, a particular pH cannot be concluded from the experiments detailed in documents EP 433 611 A1 and EP 945 429 A1.

Even though the teachings of the documents detailed above already lead to an improvement in the catalyst properties, there is a permanent need to improve the lifetime further in order to prolong the exchange cycles in continuous operation of the plants and to reduce the costs for the exchange of the catalyst. In this context, it should be emphasized that very large amounts of catalyst are required.

BRIEF SUMMARY OF THE INVENTION

In view of the prior art, it is thus an object of the present invention to provide processes for preparing carboxamides which can be performed in a particularly simple and inexpensive manner and with high yield. A particular problem has been in particular to provide a process which, with high speed, low energy conversion and low yield losses, ensures a particularly long service life of the catalyst.

This object, and further objects which are not stated explicitly but which are derivable or discernible immediately from the connections discussed by way of introduction herein, are achieved by a process having all features of claim 1. Appropriate modifications of the processes according to the invention are protected in subclaims. With regard to the process for preparing alkyl (meth)acrylates, claim 23 provides a solution to the problem underlying this object.

By virtue of the reaction mixture added to the catalyst comprising manganese dioxide having a pH in the range of 7.0 to 11.0 and the hydrolysis being performed in the presence of an oxidizing agent, it is possible to provide a process for preparing carboxamides by hydrolysing carbonitriles in the presence of a catalyst comprising manganese dioxide, which can be performed in a particularly simple and inexpensive manner and with high yield.

At the same time, the processes according to the invention can achieve a series of further advantages. One is that the process according to the invention can surprisingly greatly prolong the lifetime of the catalyst. This allows the process to be performed particularly efficiently and inexpensively, since an interruption of operation to exchange the catalyst is needed only rarely in a continuous operation of the plant.

BRIEF DESCRIPTION OF THE SEVERAL VIEWS OF THE DRAWINGS

FIG. 1 shows the configuration of a still according to one embodiment of the invention.

DETAILED DESCRIPTION OF THE INVENTION

The process according to the invention enables the efficient preparation of carboxamides. In the process, carbonitriles in particular are used, which generally have groups of the formula —CN. Carboxamides comprise at least one group of the formula —$CONH_2$. These compounds are known in the technical field and are described, for example, in Römpp Chemie Lexikon, 2nd edition on CD-ROM.

The reactants used may in particular be aliphatic or cycloaliphatic carbonitriles, saturated or unsaturated carbonitriles and aromatic and heterocyclic carbonitriles. The carbonitriles to be used as reactants may have one, two or more nitrile groups. In addition, it is also possible to use carbonitriles which have heteroatoms, especially halogen atoms such as chlorine, bromine, fluorine, oxygen, sulphur and/or nitrogen atoms in the aromatic or aliphatic radical. Particularly suitable carbonitriles preferably comprise 2 to 100, preferably 3 to 20 and most preferably 3 to 5 carbon atoms.

The aliphatic carbonitriles which each have a saturated or unsaturated hydrocarbon group include acetonitrile, propionitrile, butyronitrile, isobutyronitrile, valeronitrile, isovaleronitrile, capronitrile and other saturated mononitriles; malonitrile, succinonitrile, glutaronitrile, adiponitrile and other saturated dinitriles; α-aminopropionitrile, α-aminomethylthio-butyronitrile, α-aminobutyronitrile, aminoacetonitrile and other α-aminonitriles; cyanoacetic acid and other nitriles with one carboxyl group in each case; amino-3-propionitrile and other β-aminonitriles; acrylonitrile, methacrylonitrile, allyl cyanide, crotononitrile, other unsaturated nitriles, and cyclopentanecarbonitrile and cyclohexanecarbonitrile or other alicyclic nitriles.

The aromatic carbonitriles include benzonitrile, o-, m- and p-chlorobenzonitrile, o-, m- and p-fluorobenzo-nitrile, o-, m- and p-nitrobenzonitrile, p-aminobenzo-nitrile, 4-cyanophenol, o-, m- and p-tolunitrile, 2,4-dichlorobenzonitrile, 2,6-dichlorobenzonitrile, 2,6-difluorobenzonitrile, anisonitrile, α-naphthonitrile, β-naphthonitrile and other aromatic mononitriles: phthalonitrile, isophthalonitrile, terephthalonitrile and other aromatic dinitriles; benzylcyanide, cinnamoylnitrile, phenylacetonitrile, mandelonitrile, p-hydroxyphenylacetonitrile, p-hydroxyphenylpropio-nitrile, p-methoxyphenylacetonitrile and other nitriles which each have one aralkyl group.

The heterocyclic carbonitriles include in particular nitrile compounds which each have a heterocyclic group which contains a 5- or 6-membered ring and has at least one atom which is selected from the group consisting of a nitrogen atom, an oxygen atom and a sulphur atom as a heteroatom, for example 2-thiophenecarbonitrile, 2-furonitrile and other nitriles which each have a sulphur atom or an oxygen atom as a heteroatom; 2-cyanopyridine, 3-cyanopyridine, 4-cyanopyridine, cyanopyrazine and other nitriles which each contain a nitrogen atom as a heteroatom; 5-cyanoindole and other fused heterocycles; cyanopiperidine, cyanopiperazine and other hydrogenated heterocyclic nitriles, and fused heterocyclic nitriles.

The particularly preferred carbonitriles include in particular α-hydroxycarbonitriles (cyanohydrins), for example hydroxyacetonitrile, 2-hydroxy-4-methylthio-butyronitrile, α-hydroxy-γ-methylthiobutyronitrile (4-methylthio-2-hydroxybutyronitrile), 2-hydroxypropio-nitrile (lactonitrile) and 2-hydroxy-2-methylpropio-nitrile (acetone cyanohydrin), particular preference being given to acetone cyanohydrin.

According to the invention, the hydrolysis of the carbonitrile is performed in the presence of a catalyst comprising manganese dioxide. The stoichiometric composition of natural and synthetic manganese dioxide, by virtue of the incorporation of manganese of other valence states into the crystal lattice, may preferably be in the range between $MnO_{1.7}$ and $MnO_{2.0}$. Manganese dioxide exists in several allotropic modifications. They differ greatly in their behaviour as a catalyst. In pyrolysite (beta-manganese dioxide), the most stable modification, the crystallinity is the most marked. The crystallinity in the further modifications is less marked and extends down to amorphous products which include alpha- or delta-$MnO_2$. X-ray diffraction can be used to assign the modification. Some of the chemically and catalytically particularly active forms of manganese dioxide may be hydrated and additionally contain hydroxyl groups.

The catalyst comprising manganese dioxide may comprise further compounds or ions. These include in particular alkali metal and/or alkaline earth metal ions which are introduced into the crystal lattice in the preparation or are deposited on the surface of the catalyst. The preferred alkali metal ions include in particular lithium, sodium and/or potassium ions. The preferred alkaline earth metal ions include in particular calcium and/or magnesium ions. The content of alkali metal and/or alkaline earth metal may preferably be less than 0.6 atom per atom of manganese. The atomic ratio of alkali metal and/or alkaline earth metal to manganese is preferably in the range of 0.01:1 to 0.5:1, more preferably in the range of 0.05:1 to 0.4:1.

In addition, the catalyst comprising manganese dioxide may comprise promoters, which may likewise be introduced into the crystal lattice or be deposited on the surface of the catalyst. The preferred promoters include Ti, Zr, V, Nb, Ta, Cr, Mo, W, Zn, Ga, In, Ge, Sn and Pt. The content of promoters may preferably be less than 0.3 atom per atom of manganese. The atomic ratio of promoter to manganese is preferably in the range of 0.001:1 to 0.2:1, more preferably in the range of 0.005:1 to 0.1:1. The catalyst comprising manganese dioxide may preferably comprise 0.01 to 10% by weight, more preferably 0.1 to 5% by weight, of promoters, this parameter being based on the weight measured as the metal or metal ion.

In addition, suitable catalysts may comprise fractions of $SiO_2$ or other binders in order to increase the mechanical stability, as detailed, for example, in EP-A-0 956 898.

Particularly preferred catalysts comprise, for example, 0.0 to 25% by weight, in particular 0.1 to 2% by weight, of $SiO_2$;

0.1 to 10% by weight, in particular 2 to 7% by weight, of $K_2O$;

0.0 to 5% by weight, in particular 0.2 to 4% by weight, of $ZrO_2$ and 75 to 99% by weight, in particular 85 to 98% by weight, of $MnO_2$. The catalyst may comprise further elements as has been detailed above. The composition of the catalysts can be determined by semiquantitative X-ray fluorescence analysis.

Preferred catalysts comprising manganese dioxide have, in the X-ray spectrum (XRD) measured as the powder, at least one reflection in the range of 32.0 to 42.0°. The X-ray spectrum can be obtained, for example, with an Xpert pro system from Panalytical. This reflection in the range of 32.0 to 42.0° more preferably has the highest intensity in relation to the further intensities in the range of 20° to 65°, measured as the maximum of the reflection. Particularly preferred catalysts exhibit low crystallinity, and this can be seen, inter alia, from the X-ray spectrum. The structure of particularly preferred catalysts can be assigned to the structure 44-0141 or 72-1982, which is presented in ICDD (International Centre for Diffraction Data), particular preference being given to the crystals having a structure according to 44-0141.

The alkali metal and/or alkaline earth metal ions and the promoters may be added, for example, in the form of salts in the preparation of the catalysts. For instance, it is possible in particular to use halides, nitrates, sulphates, carbonates, phosphates and hydroxides of the aforementioned substances, preference being given to using compounds which are soluble in water.

The catalyst comprising manganese dioxide may preferably comprise at least 50% by weight, more preferably at least 80% by weight, of manganese dioxide having an empirical formula $MnO_x$ where x is in the range of 1.7 to 2.0.

In a particular aspect of the present invention, the catalyst comprising manganese dioxide may have a specific surface area (BET) in the range of 50 to 1000 m² per g, more preferably 100 to 300 m² per g and most preferably 150 to 250 m² per g, which is determined according to test method DIN66131.

Depending on the reactor type, the catalyst can be used, for example, in the form of powder or granule, the particle size in many cases being dependent upon the reaction vessel used.

The preparation of the catalysts which comprise manganese dioxide and have been described above is known per se and is detailed, for example, in EP-A-0 379 111, EP-A-0 956 898, EP-A-0545697 and EP-A-0 433 611. The catalysts which comprise manganese dioxide and are to be used in accordance with the invention can preferably be obtained by oxidation of $Mn^{2+}$ salts, for example $MnSO_4$, with permanganates, for example potassium permanganate (cf. Biochem. J., 50 p. 43(1951) and J. Chem. Soc., p. 2189, 1953). In addition, suitable manganese dioxide can be obtained by electrolytic oxidation of manganese sulphate in aqueous solution.

Catalysts with structures according to 44-0141 can be obtained, for example, by adding an aqueous solution containing 0.71 mol of Mn(II)SO$_4$ (total of 15% by weight of $Mn^{2+}$ in solution), 0.043 mol of $Zr(IV)(SO_4)_2$, 0.488 mol of conc. sulphuric acid and 13.24 mol of water at 70° C. rapidly to a solution of 1.09 mol of $KMnO_4$ in 64.5 mol of water. The supernatant solution with the precipitate formed can be heated to 90° C. for 3 hours. The precipitate can then be filtered off, washed four times with one litre of water and dried at 110° C. for 12 hours.

According to the invention, the reaction mixture added to the catalyst comprising manganese dioxide has a pH in the range of 6.0 to 11.0, preferably 6.5 to 10.0 and most preferably 8.5 to 9.5. In this context, the pH is defined as the negative decadic logarithm of the activity of the oxonium ions ($H_3O^+$). This parameter is thus dependent upon factors including the temperature, this parameter being based on the reaction temperature. For the purposes of the invention, it is in many cases sufficient to determine this parameter with electrical measuring units (pH meters), a determination at room temperature being sufficient for many purposes instead of the reaction temperature.

Without addition of an acid or base, a mixture of the reactants used customarily generally has a pH in the range of 3 to 5.5. Therefore, preference is given to adding a basic substance to adjust the pH of the reaction mixture. For this purpose, it is possible with preference to use hydroxides or oxides which are more preferably formed by alkaline earth metals or alkali metals. These include $Ca(OH)_2$ and $Mg(OH)_2$, MgO, CaO, NaOH, KOH, LiOH or $Li_2O$. Very particular preference is given here to using LiOH or $Li_2O$. Theoretically, amines can also be used to adjust the pH. However, it has been found that the use of amines can have a disadvantageous influence on the lifetime of the catalyst. The content of amines, especially for adjusting the pH in the reaction mixture, is preferably at most 0.1% by weight, more preferably at most 0.01% by weight and most preferably at most 0.001% by weight. In a particular aspect, no significant proportion of amine is added to adjust the pH of the reaction mixture.

It should be emphasized here that the catalyst comprising manganese dioxide in many cases has amphoteric properties; therefore, the pH of the reaction mixture in the reaction is greatly influenced by the type and amount of the catalyst. The expression "the reaction mixture added to the catalyst comprising manganese dioxide" makes it clear that the pH is measured without the presence of the catalyst. The further constituents of the reaction mixture include, for example, solvent, water, carbonitrile, etc.

It has been found that, surprisingly, hydrolysis in the presence of lithium ions leads to a particularly long lifetime of the catalyst comprising manganese dioxide. Accordingly, the process according to the invention can be further improved by adding lithium compounds, especially water-soluble lithium salts, to the reaction mixture, for example LiCl, LiBr, $Li_2SO_4$, LiOH and/or $Li_2O$. The concentration of lithium compounds is preferably in the range of 0.001 to 5% by weight, more preferably 0.01% by weight to 1% by weight. The addition can be effected during or before the hydrolysis reaction.

According to the invention, the hydrolysis of the carbonitrile to the carboxamide takes place in the presence of an oxidizing agent. Suitable oxidizing agents are widely known in the technical field. These oxidizing agents include oxygenous gases; peroxides, for example hydrogen peroxide ($H_2O_2$), sodium peroxide, potassium peroxide, magnesium peroxide, calcium peroxide, barium peroxide, benzoyl peroxide and diacetyl peroxide; peracids or salts of peracids, for example performic acid, peracetic acid, sodium persulphate, ammonium persulphate and potassium persulphate; and oxo acids or salts of oxo acids, for example periodic acid, potassium periodate, sodium periodate, perchloric acid, potassium perchlorate, sodium perchlorate, potassium chlorate, sodium chlorate, potassium bromate, sodium iodate, iodic acid, sodium hypochlorite, permanganate salts, for example potassium permanganate, sodium permanganate and lithium permanganate, and salts of chromic acid, for example potassium chromate, sodium chromate and ammonium chromate.

The amount of the oxidizing agent used may be within a wide range, but the reactants and products should not be oxidized by the oxidizing agent. The oxidation sensitivity of these substances may therefore limit the use of the oxidizing agents. The lower limit results from the improvement in the service life of the catalyst to be achieved. The molar ratio of oxidizing agent to carbonitrile is preferably in the range of 0.001:1 to 2:1, more preferably 0.01:1 to 1.5:1.

These oxidizing agents may be added to the reaction mixture, for example, as a solution and/or as a gas. The oxidizing agents used are more preferably gases which comprise oxygen. In this case, the gas may comprise molecular oxygen ($O_2$) or ozone ($O_3$). In addition, the gas used as an oxidizing agent may comprise further gases, especially inert gases, such as nitrogen or noble gases. In a particular aspect, the gas may comprise preferably 50 to 98% by volume of inert gas and 2 to 50% by volume of molecular oxygen ($O_2$). The preferred gases include in particular air. In addition, it is also possible to use a gas which contains less than 20% by volume, in particular less than 10% by volume, of molecular oxygen, these gases containing generally at least 1% by volume, preferably at least 2% by volume, of oxygen.

The amount of gas which comprises oxygen and is passed through the reaction mixture may preferably be in the range of 1 to 5000 litres/hour, more preferably in the range of 10 to 1000 litres/hour, based on 1 kg of catalyst comprising manganese dioxide.

The water which is needed to hydrolyse the carbonitrile may in many cases be used as the solvent. The molar ratio of water to carbonitrile is preferably at least 1; the molar ratio of water to carbonitrile is more preferably in the range of 0.5:1-25:1 and most preferably in the range of 1:1-10:1.

The water used for the hydrolysis may have a high purity. However, this property is not obligatory. As well as fresh water, it is thus also possible to use service water or process water which comprises greater or lesser amounts of impurities. Accordingly, it is also possible to use recycled water for the hydrolysis.

In addition, further constituents may be present in the reaction mixture for the hydrolysis of the carbonitrile. These include carbonyl compounds such as aldehydes and ketones, especially those which have been used to prepare cyanohydrins to be used with preference as the carbonitrile. For example, acetone and/or acetaldehyde may be present in the reaction mixture. This is described, for example, in U.S. Pat. No. 4,018,829-A. The purity of the aldehydes and/or ketones added is generally not particularly critical. Accordingly, these substances may comprise impurities, especially alcohols, for example methanol, water and/or methyl α-hydroxyisobutyrate (MHIB). The amount of carbonyl compounds, especially acetone and/or acetaldehyde, may be set within wide ranges in the reaction mixture. The carbonyl compound is preferably used in an amount of 0.1-6 mol, preferably 0.1-2 mol, per mole of carbonitrile.

The temperature at which the hydrolysis reaction is effected may generally be in the range of 10-150° C., preferably in the range of 20-100° C. and more preferably in the range of 30-80° C.

Depending on the reaction temperature, the hydrolysis reaction can be performed at reduced or elevated pressure. Preference is given to performing this reaction in a pressure range of 0.1-10 bar, more preferably 0.5 to 5 bar.

The reaction time of the hydrolysis reaction depends upon factors including the carbonitriles used, the activity of the catalyst and the reaction temperature, and these parameters may be within wide ranges. The reaction time of the hydrolysis reaction is preferably in the range of 30 seconds to 15 hours, more preferably 15 minutes to 10 hours and most preferably 60 minutes to 5 hours.

In continuous processes, the residence time is 30 seconds to 15 hours, more preferably 15 minutes to 10 hours and most preferably 60 minutes to 5 hours.

The loading of the catalyst with carbonitrile may be within a wide range. Preference is given to using 0.01 to 2.0 g, more preferably 0.05 to 1.0 g and most preferably 0.1 to 0.4 g, of carbonitrile per g of catalyst per hour.

The reaction may be performed, for example, in a fixed bed reactor or in a suspension reactor. If gases are used as oxidizing agents, it is possible in particular to use so-called trickle bed reactors which enable good contact of gas, solid and liquid. In trickle bed reactors, the catalyst is arranged in the form of a fixed bed. In this case, the trickle bed reactor can be operated in cocurrent or countercurrent mode.

The reaction mixture thus obtained can generally, as well as the desired carboxamide, comprise further constituents, especially unconverted carbonitrile and any acetone and/or acetaldehyde use. Accordingly, the reaction mixture can be purified, which can, for example, split unconverted cyanohydrin into acetone and hydrocyanic acid, in order to use them again for the preparation of the cyanohydrin. The same applies to the acetone and/or acetaldehyde removed.

In addition, the purified reaction mixture comprising carboxamide can be purified to remove further constituents by ion exchange columns.

For this purpose, it is possible in particular to use cation exchangers and anion exchangers. Ion exchangers suitable for this purpose are known per se. For example, suitable cation exchangers can be obtained by sulphonating styrene-divinylbenzene copolymers. Basic anion exchangers comprise quaternary ammonium groups which are bonded covalently to styrene-divinylbenzene copolymers.

The purification of α-hydroxycarboxamides is described in detail, inter alia, in EP-A-0686623.

The carbonitrile used for the hydrolysis may be obtained in any way. In the process according to the invention, the purity of the carbonitrile, for example of the cyanohydrin, is generally uncritical. Accordingly, purified or unpurified carbonitrile can be used for the hydrolysis reaction.

To prepare cyanohydrins to be used with preference, it is possible, for example, to react a ketone, especially acetone, or an aldehyde, for example acetaldehyde, propanal, butanal, with hydrocyanic acid to give the corresponding cyanohydrin. Particular preference is given here to reacting acetone and/or acetaldehyde in a typical manner using a small amount of alkali or of an amine as a catalyst. The amines used to catalyse this reaction may preferably be used in the form of basic ion exchange resins.

Accordingly, the carbonitrile can preferably be obtained by reacting a ketone or aldehyde with hydrocyanic acid in the presence of a basic catalyst. In a particular embodiment, the basic catalyst used may be an alkali metal hydroxide, the amount of basic catalyst preferably being selected such that the pH of the mixture used for the hydrolysis reaction is adjusted to a value in the range of 6.0 to 11.0, preferably 6.5 to 10.0 and most preferably 8.5 to 9.5.

The hydrolysis reaction of the present invention may in particular serve as an intermediate step in processes for preparing (meth)acrylic acids, in particular acrylic acid (propenoic acid) and methacrylic acid (2-methylpropenoic acid) and of alkyl (meth)acrylates. Accordingly, the present invention also provides a process for preparing methyl methacrylate which has a hydrolysis step according to a process of the present invention. Processes which may have a hydrolysis step of cyanohydrins to prepare (meth)acrylic acid and/or alkyl (meth)acrylates are detailed, inter alia, in EP-A-0 406 676, EP-A-0 407 811, EP-A-0 686 623 and EP-A-0 941 984.

In a particularly preferred embodiment, it is possible to obtain alkyl (meth)acrylates from carbonyl compounds, hydrocyanic acid and alcohols in a simple and inexpensive manner by processes which comprise the following steps:
A) formation of at least one cyanohydrin by reacting at least one carbonyl compound with hydrocyanic acid;
B) hydrolysis of the cyanohydrin or of the cyanohydrins to form at least one α-hydroxycarboxamide;
C) alcoholysis of the α-hydroxycarboxamide or of the α-hydroxycarboxamides to obtain at least one alkyl α-hydroxycarboxylate;
D) transesterification of the alkyl α-hydroxycarboxylate or of the alkyl α-hydroxycarboxylates with (meth)acrylic acid to form at least one alkyl (meth)acrylate and at least one α-hydroxycarboxylic acid;
E) dehydration of the α-hydroxycarboxylic acid or of the α-hydroxycarboxylic acids to form (meth)acrylic acid.

Steps A) and B) have been explained in detail above. In the next step C), the α-hydroxycarboxamide thus obtained can be converted to the alkyl α-hydroxycarboxylate. This can be done, for example, by the use of alkyl formates. An especially suitable reactant is methyl formate or a mixture of methanol and carbon monoxide, this reaction being described by way of example in EP-A-0407811.

Preference is given to reacting the α-hydroxycarboxamide by alcoholysis with an alcohol which comprises preferably 1-10 carbon atoms, more preferably to 5 carbon atoms. Preferred alcohols include methanol, ethanol, propanol, butanol, especially n-butanol and 2-methyl-1-propanol, pentanol, hexanol, heptanol, 2-ethylhexanol, octanol, nonanol and decanol.

The alcohol used is more preferably methanol and/or ethanol, very particular preference being given to methanol. The reaction of carboxamides with alcohols to obtain carboxylic esters is common knowledge.

The molar ratio of α-hydroxycarboxamide to alcohol, for example α-hydroxyisobutyramide to methanol, is not critical per se, and is preferably in the range of 1:3 to 20:1. This ratio is very particularly appropriately in the range of 1:2 to 15:1 and more preferably in the range of 1:1 to 10:1.

The reaction temperature may likewise be within wide ranges, the reaction rate generally increasing with increasing temperature. The upper temperature limit arises generally from the boiling point of the alcohol used. The reaction temperature is preferably in the range of 40-300° C., more preferably 160-240° C. The reaction may, depending on the reaction temperature, be performed at reduced or elevated pressure. This reaction is preferably performed in a pressure range of 0.5 to 200 bar, particularly appropriately in a range of 1 to 100 bar and more preferably 5 to 30 bar.

In a particular embodiment, the reaction between α-hydroxycarboxamide and alcohol can be performed in a pressure reactor. This is in principle understood to mean a reaction chamber which permits an elevated pressure to be maintained during the reaction. In this context, elevated pressure means a pressure greater than atmospheric pressure, i.e. in particular greater than 1 bar. The pressure may preferably be in the range of greater than 1 bar to less than 100 bar. Accordingly, the pressure, both during the reaction/alcoholysis of alpha-hydroxycarboxamide and during the removal of the ammonia from the product mixture, may be greater than atmospheric pressure or greater than 1 bar. Therefore, the ammonia formed in the reaction can be distilled out of the mixture under a pressure of greater than 1 bar, and it is possible to completely dispense with the use of aids such as stripping gas for the distillative removal of the ammonia.

The product mixture may be depleted not only in ammonia but also in unconverted alcohol. Specifically in the case that methanol is used for the alcoholysis, the result is a product mixture comprising, inter alia, the components ammonia and methanol which are in principle very difficult to separate from one another. In the simplest case, the product mixture is depleted in ammonia and alcohol by removing said two components directly as a substance mixture from the product mixture. The two substances are then subjected to a separating operation, for example a rectification. In addition, the two components alcohol (methanol) and ammonia can be separated from the product mixture in one operation, and the two constituents ammonia and alcohol (methanol) can at the same time be separated from one another.

The reaction step and the removal of the ammonia/alcohol from the product mixture can be performed spatially separately from one another and in different units. For this purpose, it is possible, for example, to provide one or more pressure reactors and to connect them to a pressure distillation column. This system comprises one or more reactors which are arranged outside the column in a separate region.

Preference may be given to employing a continuous process for preparing alpha-hydroxycarboxylic esters in which alpha-hydroxycarboxamide reactants are reacted with an alcohol in the presence of a catalyst to obtain a product mixture which comprises alpha-hydroxycarboxylic ester, ammonia, unconverted alpha-hydroxycarboxamide, and alcohol and catalyst; by
a') feeding reactant streams comprising, as reactants, an alpha-hydroxycarboxamide, an alcohol and a catalyst into a pressure reactor;
b') reacting the reactant streams with one one another in the pressure reactor at a pressure in the range of greater than 1 bar to 100 bar;
c') discharging the product mixture which results from step b') and comprises alpha-hydroxycarboxylic ester, unconverted alpha-hydroxycarboxamide and catalyst from the pressure reactor; and
d') depleting the product mixture in alcohol and ammonia, ammonia being distilled off at a pressure which is constantly kept greater than 1 bar.

In this case, a particularly appropriate process modification can be provided by
b1) reacting the reactants with one another in the pressure reactor at a pressure in the range of 5 bar to 70 bar;
b2) decompressing the product mixture resulting from step b1) to a pressure less than the pressure in the pressure reactor and greater than 1 bar;
c1) feeding the decompressed product mixture which results from step b2) into a distillation column;
c2) in the distillation column, distilling off alcohol and ammonia via the top, the pressure in the distillation column being kept in the range of greater than 1 bar to less than 10 bar; and
d1) discharging the product mixture which results from step c2), has been depleted in ammonia and alcohol, and comprises alpha-hydroxycarboxylic ester, unconverted alpha-hydroxycarboxamide and catalyst from the column.

In this preferred process variant, reaction of the reactants and removal of ammonia/alcohol take place in two different spatially separate units. In other words, reactor/reaction chamber and separating unit for the removal of ammonia/alcohol from the product mixture are separated from one another. This has the advantage that, for the reaction of the reactants and the subsequent removal of ammonia/alcohol, different pressure ranges can be employed. The separation of the process into a reaction step in the pressure reactor under higher pressure than in a separating step in a pressure column, both steps being conducted under elevated pressure, i.e. greater than 1 bar, surprisingly allows the separating action to be improved significantly once more and the efficiency of the removal of the ammonia/alcohol mixture to be increased.

The quality features mentioned can be improved even further by repeating the reaction in the pressure reactor once or more than once with the product mixture which has been depleted in ammonia and alcohol in the bottom of the separating column (pressure distillation column), the reaction step being shifted to a multitude of pressure reactors which are connected in series.

In this respect, very particular preference is given to a process variant which is characterized in that e) the product mixture discharged in step d1) is compressed to a pressure in the range of 5 to 70 bar;
f) the mixture compressed in this way in step e) is fed into a further pressure reactor for reaction and allowed to react again; and
g) steps b2), c1), c2) and d1) are repeated according to the list above.

Accordingly, it is of particular interest that the mixture depleted in ammonia and alcohol is withdrawn from a tray above the bottom of the first distillation column, compressed to a pressure greater than in the distillation column and then fed into a second pressure reactor, whence, after another reaction under the action of elevated pressure and temperature to obtain a twice-reacted product mixture, it is decompressed to a pressure less than in the second pressure reactor and greater than 1 bar, and then recycled into the first distillation column below the tray from which the feeding into the second pressure reactor was effected but above the bottom of the first distillation column, where ammonia and alcohol are distilled off again via the top to obtain a mixture depleted twice in ammonia and alcohol.

This process step can be repeated as desired; for example, three to four repetitions are particularly favourable. In this respect, particular preference is given to a process which is characterized in that the reaction in the pressure reactor, the decompression of the reacted mixture, the feeding into the first distillation column, the depletion of ammonia and alcohol in the first distillation column, the withdrawal of the depleted mixture, compression and feeding of the depleted mixture into a further pressure reactor are repeated more than once to obtain, depending on the number n of pressure reactors connected in series, a product mixture depleted n times in ammonia and alcohol at the bottom of the pressure distillation column. n may be a positive integer greater than zero. n is preferably in the range of 2 to 10.

An appropriate process modification envisages repeating the steps e) to g) mentioned and defined above more than once.

Very specific process variants comprise the performance of the reaction and depletion four times using four pressure reactors connected in series to obtain a product mixture depleted four times in ammonia and alcohol. This process variant is accordingly characterized in that steps e) to g) are repeated at least twice more, so that the reaction is performed in a total of at least four pressure reactors connected in series.

For the process variants specified, different temperature ranges have been found to be particularly appropriate in column and reactor.

For example, the pressure distillation column may generally and preferably have a temperature in the range of about 50° C. to about 160° C. The exact temperature is typically established by the boiling system as a function of the existing pressure conditions.

The temperature in the reactor is preferably in the range of about 120-240° C. It is very particularly appropriate to lower the temperature from reactor to reactor, for example in steps in the range of 3-15° C., preferably 4-10° C. and very particularly appropriately in steps of 5° C. This positively influences the selectivity of the reaction.

A further measure for increasing the selectivity may also consist in decreasing the reactor volume from reactor to reactor. Decreasing reactor volume with increasing conversion likewise affords improved selectivity.

As already mentioned above, it is favourable to withdraw the product mixture to be withdrawn from the pressure distillation column at certain points in the column. In this context, for orientation, as a relative statement of location, the distance of the withdrawal point from the bottom of the column is used. Particularly appropriately, the procedure in the context of the invention is to feed the decompressed product mixture according to step c1) after each new reaction into a pressure reactor more closely adjacent to the bottom of the distillation column based on the feed point of the feeding of the preceding step c1).

In addition to the variants described, in which the reaction of the alpha-hydroxycarboxamide with the alcohol is performed by the removal of the ammonia which is one resulting product in two spatially separate but connected units, it may be preferred in a further process modification to undertake the reaction step and the removal step in a single unit. In this case, pressure reactor and pressure distillation column are realized in a single unit, and effectively coincide.

The pressure range to be observed in the inventive variants described above, preferably in a reactive distillation column serving as a reactor, is variable over wide ranges. A preferred embodiment of the invention comprises the performance of steps a) to c) simultaneously in a reactive distillation column at a pressure in the range of 5 bar to 40 bar. A particularly appropriate process is one which is characterized in that steps a) to c) are performed simultaneously in a reactive distillation column at a pressure in the range of 10 bar to 30 bar.

In a preferred variant of the process, the reaction of the reactants is performed in a reactive distillation column designed as a pressure column, and the ammonia formed is distilled off continuously via the top of the column during the reaction. This achieves the surprising effect that ammonia can be removed in a very simple manner without needing to reduce the pressure and can be recovered in high purity. Another variant of particular interest is one in which ammonia is distilled off under pressure via the top of the column and the alcohol is removed from the column via the bottom or via a sidestream. As a result of an appropriately configured separating action of the reactive distillation column, immediate separation of ammonia and alcohol is thus achieved.

For the present invention, in one variant, any multistage pressure-resistant reactive distillation column which preferably has two or more separating stages can be used. Such reactive stills are explained in detail in connection with step D), and these can also be used for the reaction of the carboxamide with an alcohol.

The product mixture depleted in ammonia contains, inter alia, the desired alpha-hydroxycarboxylic ester. To further isolate and purify the ester, it is possible in an appropriate process modification to draw off the product mixture depleted in ammonia via the bottom of the reactive distillation column and to feed it to a further second distillation column, where the alcohol is distilled off via the top of the column and preferably recycled into a reactor to obtain a mixture depleted in both ammonia and alcohol.

To further isolate and recover the alpha-hydroxycarboxylic ester from the mixture depleted in ammonia and alcohol, preference is then given to a process in which the mixture depleted in ammonia and alcohol is discharged via the bottom of the further distillation column and fed to yet a further distillation column in which the alpha-hydroxycarboxylic ester is distilled off via the top and the thus obtained mixture depleted in ammonia, alcohol and alpha-hydroxycarboxylic ester, optionally after further purification steps, is recycled into the reactor. The alpha-hydroxycarboxylic ester product obtained via the top of the column is highly pure and can, for example, be fed extremely advantageously to further reaction steps to obtain alkyl(meth)acrylates.

As outlined, the distillation apparatus preferably has at least one region, known as reactor, in which at least one catalyst is provided. This reactor can, as described, preferably be within the distillation column.

For the invention, it may be advantageous when at most 10% by weight, preferably at most 5% by weight and more preferably at most 1% by weight of the alcohol present in the reaction phase is removed from the reaction system via the gas phase. This measure allows the reaction to be performed particularly inexpensively.

This reaction can be accelerated, for example, by basic catalysts. These include homogeneous catalysts and heterogeneous catalysts.

The homogeneous catalysts include alkali metal alkoxides and organometallic compounds of titanium, tin and aluminium. Preference is given to using a titanium alkoxide or tin alkoxide, for example titanium tetra-isopropoxide or tin tetrabutoxide. The heterogeneous catalysts include magnesium oxide, calcium oxide and basic ion exchangers as have been described above.

Catalysts of very particular interest for the performance of the process according to the invention are water-resistant lanthanoid compounds. The use of this type of homogeneous catalysts leads to particularly surprising results. The expression "water-resistant" means that the catalyst retains its catalytic abilities in the presence of water. Accordingly, the inventive reaction can be effected in the presence of up to 2% by weight of water without this significantly impairing the catalytic ability of the catalyst. In this context, the expression "significantly" means that the reaction rate and/or selectivity decreases at most by 50% based on the reaction without the presence of water.

Lanthanoid compounds denote compounds of La, Ce, Pr, Nd, Pm, Sm, Eu, Gd, Tb, Dy, Ho, Er, Tm, Yb and/or Lu. Preference is given to using a lanthanoid compound which comprises lanthanum.

The lanthanoid compound preferably has a solubility in water of at least 1 g/l, preferably at least 10 g/l, at 25° C.

Preferred lanthanoid compounds are salts which are preferably present in the oxidation state 3.

Particularly preferred water-resistant lanthanoid compounds are $La(NO_3)_3$ and/or $LaCl_3$. These compounds may be added to the reaction mixture as salts or be formed in situ.

A particular process variant includes the use, as a catalyst, of a soluble metal complex which comprises titanium and/or tin and the alpha-hydroxycarboxamide.

Another specific modification of the invention envisages the use of a metal trifluoromethanesulphonate as a catalyst. In this case, preference is given to using a metal trifluoromethanesulphonate in which the metal is selected from the group consisting of the elements in groups 1, 2, 3, 4, 11, 12, 13 and 14 of the Periodic Table. Among these, preference is given to those metal trifluoromethanesulphonates in which the metal corresponds to one or more lanthanoids.

In addition to the preferred variants of homogeneous catalysis, processes using heterogeneous catalysts are also appropriate under some circumstances. The successfully usable heterogeneous catalysts include magnesium oxide, calcium oxide and basic ion exchangers, and the like.

For example, preference may be given to processes in which the catalyst is an insoluble metal oxide which comprises at least one element selected from the group consisting of Sb, Sc, V, La, Ce, Ti, Zr, Hf, Nb, Ta, Cr, Mo, W, Tc, Re, Fe, Co, Ni, Cu, Al, Si, Sn, Pb and Bi.

Alternatively, preference may be given to processes where the catalyst used is an insoluble metal selected from the group consisting of Ti, Zr, Hf, V, Nb, Ta, Cr, Mo, W, Fe, Co, Ni, Cu, Ga, In, Bi and Te.

Typically, the ammonia formed is discharged from the reaction system, the reaction in many cases being performed at the boiling point.

The ammonia released in the alcoholysis may be recycled easily to the overall process. For example, ammonia may be reacted with methanol to give hydrocyanic acid. This is detailed, for example, in EP-A-0941984. In addition, the hydrocyanic acid can be obtained from ammonia and methane by the BMA or Andrussow processes, these processes being described in Ullmann's Encyclopedia of Industrial Chemistry, 5th Edition on CD-ROM, under "Inorganic Cyano Compounds".

In a next step D), the alkyl α-hydroxycarboxylate is reacted with (meth)acrylic acid to obtain alkyl (meth)acrylate and α-hydroxycarboxylic acid.

In the further aspect of the present invention, alkyl α-hydroxycarboxylates can be reacted with (meth)acrylic acid. The (meth)acrylic acids usable for this purpose are known per se and can be obtained commercially. In addition to acrylic acid (propenoic acid) and methacrylic acid (2-methylpropenoic acid), these include in particular derivatives which comprise substituents. The suitable substituents include in particular halogens such as chlorine, fluorine and bromine, and alkyl groups which may comprise preferably 1 to 10, more preferably 1 to 4 carbon atoms. These include β-methylacrylic acid (butenoic acid), α,β-dimethylacrylic acid, β-ethylacrylic acid and β,β-dimethylacrylic acid. Preference is given to acrylic acid (propenoic acid) and methacrylic acid (2-methyl-propenoic acid), particular preference being given to methacrylic acid.

The alkyl α-hydroxycarboxylates used for this purpose are known per se, the alcohol radical of the ester comprising preferably 1 to 20 carbon atoms, in particular 1 to 10 carbon atoms and more preferably 1 to 5 carbon atoms. Preferred alcohol radicals derive in particular from methanol, ethanol, propanol, butanol, in particular n-butanol and 2-methyl-1-propanol, pentanol, hexanol and 2-ethylhexanol, particular preference being given to methanol and ethanol.

The acid radical of the alkyl α-hydroxycarboxylates used for the transesterification derives preferably from the (meth) acrylic acid which can be obtained by dehydrating the α-hydroxycarboxylic acid. When, for example, methacrylic acid is used, α-hydroxyisobutyric ester is used. When, for example, acrylic acid is used, preference is given to using α-hydroxyisopropionic acid.

Alkyl α-hydroxycarboxylates used with preference are methyl α-hydroxypropionate, ethyl α-hydroxypropionate, methyl α-hydroxyisobutyrate and ethyl α-hydroxyisobutyrate.

In addition to the reactants, the reaction mixture may comprise further constituents, for example solvents, catalysts, polymerization inhibitors and water.

The reaction of alkylhydroxycarboxylic ester with (meth)acrylic acid can be catalysed by at least one acid or at least one base. It is possible to use either homogeneous or heterogeneous catalysts. Particularly suitable acidic catalysts are in particular inorganic acids, for example sulphuric acid or hydrochloric acid, and organic acids, for example sulphonic acids, in particular p-toluenesulphonic acid, and acid cation exchangers.

The particularly suitable cation exchange resins include in particular sulphonic acid-containing styrene-divinylbenzene polymers. Particularly suitable cation exchange resins can be obtained commercially from Rohm & Haas under the trade name Amberlyst® and from Lanxess under the trade name Lewatit®.

The concentration of catalyst is preferably in the range of 1 to 30% by weight, more preferably 5 to 15% by weight, based on the sum of the α-alkylhydroxycarboxylic ester used and of the (meth)acrylic acid used.

The polymerization inhibitors usable with preference include phenothiazine, tert-butyl catechol, hydroquinone monomethyl ether, hydroquinone, 4-hydroxy-2,2,6,6-tetramethylpiperidinooxyl (TEMPOL) or mixtures thereof; the effectiveness of these inhibitors can be improved in some cases by using oxygen. The polymerization inhibitors may be used in a concentration in the range of 0.001 to 2.0% by weight, more preferably in the range of 0.01 to 0.2% by weight, based on the sum of the α-alkylhydroxycarboxylic ester used and of the (meth)acrylic acid used.

The reaction is performed preferably at temperatures in the range of 50° C. to 200° C., more preferably 70° C. to 130° C., in particular 80° C. to 120° C. and most preferably 90° C. to 110° C.

The reaction can be performed at reduced or elevated pressure depending on the reaction temperature. This reaction is preferably performed in the pressure range of 0.02-5 bar, in particular 0.2 to 3 bar and more preferably 0.3 to 0.5 bar.

The molar ratio of (meth)acrylic acid to the alkyl α-hydroxycarboxylate is preferably in the range of 4:1-1:4, in particular 3:1 to 1:3 and more preferably in the range of 2:1-1:2.

The selectivity is preferably at least 90%, more preferably 98%. The selectivity is defined as the ratio of the sum of amounts of alkyl (meth)acrylates and α-hydroxycarboxylic acids formed based on the sum of the amounts of alkyl α-hydroxycarboxylates and (meth)acrylic acid converted.

In a particular aspect of the present invention, the transesterification can be effected in the presence of water. The water content is preferably in the range of 0.1-50% by weight, more preferably 0.5-20% by weight and most preferably 1-10% by weight, based on the weight of the alkyl α-hydroxycarboxylate used.

The addition of small amounts of water surprisingly allows the selectivity of the reaction to be increased. In spite of water addition, the formation of methanol can be kept surprisingly low. At a water concentration of 10 to 15% by weight based on the weight of the alkyl α-hydroxycarboxylate used, less than 5% by weight of methanol forms at a reaction temperature of 120° C. and a reaction time or residence time of 5 to 180 min.

The transesterification can be performed batchwise or continuously, preference being given to continuous processes. In the transesterification, the products can preferably be removed from the reactants in order to shift the equilibrium of the reaction.

The reaction time of the transesterification depends upon the molar masses used and on the reaction temperature, and these parameters may be within wide ranges. The reaction time of the transesterification of the alkyl α-hydroxycarboxylate with (meth)acrylic acid is preferably in the range of 30 seconds to 15 hours, more preferably 5 minutes to 5 hours and most preferably 15 minutes to 3 hours.

In continuous processes, the residence time is preferably 30 seconds to 15 hours, more preferably 5 minutes to 5 hours and most preferably 15 minutes to 3 hours.

In the preparation of methyl methacrylate from methyl α-hydroxyisobutyrate, the temperature is preferably 60 to 130° C., more preferably 80 to 120° C. and most preferably 90 to 110° C. The pressure is preferably in the range of 50 to 1000 mbar, more preferably 300 to 800 mbar. The molar ratio of methacrylic acid to methyl α-hydroxyisobutyrate is preferably in the range of 2:1-1:2, in particular 1.5:1-1:1.5.

In a particularly preferred embodiment, the transesterification can be effected in a still. In this case, the catalyst can be added in any region of the still. For example, the catalyst can be provided in the region of the bottom or in the region of the column. At the same time, however, the reactants should be brought into contact with the catalyst. In addition, catalysts may be provided in a separate region of the still, in which case this region is connected to the further regions of the still, for example the bottom and/or the column. This separate arrangement of the catalyst region is preferred.

This preferred embodiment surprisingly succeeds in increasing the selectivity of the reaction. In this context, it should be emphasized that the pressure of the reaction can be adjusted independently of the pressure within the distillation columns. This allows the boiling temperature to be kept low without the reaction time or the residence time rising correspondingly. In addition, the temperature of the reaction can be varied over a wide range. This allows the reaction time to be shortened. In addition, the volume of catalyst can be selected as desired without needing to take account of the geometry of the column. Furthermore, for example, a further reactant can be added. All of these measures can contribute to the increase in the selectivity and the productivity, surprising synergistic effects being achieved.

In this process, the alkyl α-hydroxycarboxylate, for example methyl α-hydroxyisobutyrate, is fed to the still. In addition, (meth)acrylic acid, for example methacrylic acid, is introduced into the still. The distillation conditions are preferably configured in such a way that exactly one product is discharged from the still by distillation, the second product remaining in the bottom and being removed continuously therefrom. In the case of use of alcohols with a low carbon number, especially ethanol or methanol, preference is given to withdrawing the alkyl (meth)acrylate from the reaction mixture by distillation. The reactants are passed cyclically through the catalyst region. This continuously forms alkyl (meth)acrylate and α-hydroxycarboxylic acid.

A preferred embodiment of a still is shown schematically in FIG. 1. The reactants may be introduced into the distillation column (3) via one common line (1) or separately via two lines (1) and (2). The reactants are preferably added via separate lines. The reactants can be fed to the column at the same stage or in any position.

The temperature of the reactants can be adjusted by means of a heat exchanger in the feed, the units needed for this purpose not being shown in FIG. 1. In a preferred variant, the reactants are metered separately into the column, the lower-boiling components being metered in below the position for the feeding of the higher-boiling compounds. In this case, the lower-boiling component is preferably added in vaporous form.

For the present invention, any multistage distillation column (3) which has two or more separating stages may be used. The number of separating stages used in the present invention is the number of trays in a tray column or the number of theoretical plates in the case of a column with structured packing or a column with random packings.

Examples of a multistage distillation column with trays include those such as bubble-cap trays, sieve trays, tunnel-cap trays, valve trays, slot trays, slotted sieve trays, bubble-cap sieve trays, jet trays, centrifugal trays; for a multistage distillation column with random packings, those such as Raschig rings, Lessing rings, Pall rings, Berl saddles, Intalox saddles; and, for a multistage distillation column with structured packings, those such as Mellapak (Sulzer), Rombopak (Kühni), Montz-Pak (Montz) and structured packings with catalyst pockets, for example Kata-Pak.

A distillation column with combinations of regions of trays, of regions of random packings or of regions of structured packings may likewise be used.

The column (3) may be equipped with internals. The column preferably has a condenser (12) for condensing the vapour and a bottom evaporator (18).

The distillation apparatus preferably has at least one region, known hereinafter as reactor, in which at least one catalyst is provided. This reactor may be within the distillation column. However, this reactor is preferably arranged outside the column (3) in a separate region, one of these preferred embodiments being explained in detail in FIG. 1.

In order to carry out the transesterification reaction in a separate reactor (8), it is possible within the column to collect a portion of the liquid phase flowing downwards by means of a collector and to pass it out of the column as a substream (4). The position of the collector is determined by the concentration profile in the column of the individual components. The concentration profile can be regulated by means of the temperature and/or the reflux. The collector is preferably positioned such that the stream conducted out of the column contains both reactants, more preferably the reactants in sufficiently high concentration and most preferably in a molar acid:ester ratio=1.5:1 to 1:1.5. In addition, a plurality of collectors may be provided at various points in the distillation column, in which case the amount of reactants withdrawn can be used to adjust the molar ratios.

It is additionally possible for a further reactant, for example water, to be metered into the stream conducted out of the column, in order to adjust the acid/ester product ratio in the cross-transesterification reaction or to increase the selectivity. The water can be fed from outside via a line (not shown in FIG. 1) or withdrawn from a phase separator (13). The pressure of the stream (5) enriched with water can then be increased by a means for pressure increase (6), for example a pump.

An increase in the pressure can reduce or prevent formation of steam in the reactor, for example a fixed bed reactor. This allows uniform flow through the reactor and wetting of the catalyst particles. The stream can be conducted through a heat exchanger (7) and the reaction temperature adjusted. The stream can be heated or cooled as required. It is additionally possible to adjust the ester to acid product ratio via the reaction temperature.

The transesterification reaction takes place over the catalyst in the fixed bed reactor (8). The flow through the reactor may be downwards or upwards. The reactor output stream (9) comprising the products and the unconverted reactants to a certain degree, the content of the components in the reactor waste stream depending upon the residence time, the catalyst mass, the reaction temperature and the reactant ratio and the amount of water added, is first passed through a heat exchanger (10) and adjusted to a temperature which is advantageous for the introduction into the distillation column. Preference is given to setting the temperature which corresponds to the temperature in the distillation column at the point of introduction of the stream.

The position where the stream leaving the reactor is returned into the column may lie above or below the position for the withdrawal of the reactor feed, but will preferably be above it. Before the recycling into the column, the stream may be decompressed through a valve (11), which preferably establishes the same pressure level as in the column. In this context, the distillation column preferably has a lower pressure. This configuration offers the advantage that the boiling points of the components to be separated are lower, as a result of which the distillation can be carried out at a lower temperature level, as a result of which it saves energy and is more thermally gentle.

In the distillation column (3), the product mixture is then separated. The low boiler, preferably the ester formed in the transesterification, is removed via the top. The distillation column is preferably operated such that the water added upstream of the fixed bed reactor is likewise removed as the top product. The vaporous stream drawn off at the top is condensed in a condenser (12) and then separated in a decanter (13) into the aqueous phase and product ester-containing phase. The aqueous phase can be discharged to the workup via the line (15) or returned fully or partly back into the reaction via line (17). The stream of the ester-containing phase can be conducted via line (14) partly as reflux (16) to the column or discharged partly from the still. The high boiler, preferably the acid formed in the cross-transesterification, is discharged from the column (19) as a bottom stream.

The α-hydroxycarboxylic acid obtained from the reaction, for example hydroisobutyric acid, can be dehydrated in a known manner in a further step E). In general, the α-hydroxycarboxylic acid, for example the α-hydroxyisobutyric acid, is heated in the presence of at least one metal salt, for example of alkali metal and/or alkaline earth metal salts, to temperatures in the range of 160-300° C., more preferably in the range of 200 to 240° C., generally to obtain the (meth)acrylic acid and water. The suitable metal salts include sodium hydroxide, potassium hydroxide, calcium hydroxide, barium hydroxide, magnesium hydroxide, sodium sulphite, sodium carbonate, potassium carbonate, strontium carbonate, magnesium carbonate, sodium bicarbonate, sodium acetate, potassium acetate and sodium dihydrogenphosphate.

The dehydration of the α-hydroxycarboxylic acid can be performed preferably at a pressure in the range of 0.05 bar to 2.5 bar, more preferably in the range of 0.1 bar to 1 bar.

The dehydration of α-hydroxycarboxylic acids is described, for example, in DE-A-176 82 53.

The (meth)acrylic acid thus obtained can in turn be used to prepare alkyl (meth)acrylates. In addition, (meth)acrylic acid is a commercial product. Surprisingly, the process for preparing alkyl (meth)acrylates can accordingly likewise serve to prepare (meth)acrylic acid, in which case the product ratio of alkyl (meth)acrylates to (meth)acrylic acid can be regulated easily by the concentration of water in the transesterification of the alkyl α-hydroxycarboxylate and/or by the reaction temperature.

The present invention will be illustrated in detail hereinafter with reference to examples and to a comparative example.

COMPARATIVE EXAMPLE 1

In a beaker, 800 g of water were heated to 60° C. With stirring, 3.27 g of $Zr(SO_4)_2.4H_2O$ were dissolved. 100 g of commercially available manganese dioxide which had a BET surface area of approx. 230 $m^2/g$ and a structure number of 44-0141 according to ICDD and whose X-ray spectrum (XRD) exhibited a reflection with maximum intensity in the range of 32° to 42° were added slowly to this solution. The resulting composition was stirred at 60° C. for 2 hours. Subsequently, the manganese dioxide was removed and dried at 110° C. The dried catalyst exhibited a Zr/Mn atomic ratio of 0.008 in the X-ray fluorescence spectrum (XFA).

In a reactor, a mixture of acetone cyanohydrin, water and acetone was reacted with the above-described manganese dioxide catalyst at a temperature of 60° C. and at standard pressure. The reaction mixture was stirred. The mixing ratio of the acetone cyanohydrin-/acetone/water components was 1/1.5/15. The loading of the catalyst was approx. 0.32 to 0.36 g of acetone cyanohydrin per g of catalyst per hour.

The reaction mixture added to the catalyst had a pH of approx. 4.1. In addition, approx. 100 ml of air per minute were passed through the reaction mixture at a pressure of approx. 1 bar, and the amount of catalyst was approx. 50 g. The lifetime achieved in this experiment was approx. 8 days, the lifetime being defined as the time until the conversion falls below 50% of the starting conversion.

COMPARATIVE EXAMPLE 2

Comparative Example 1 was essentially repeated, except that the reaction mixture added to the catalyst had a pH of 9.3. In this case, the pH was adjusted by adding LiOH. In addition, nitrogen was passed through the reaction mixture instead of air.

The lifetime achieved in this experiment was approx. 9 days.

EXAMPLE 1

Comparative Example 1 was essentially repeated, except that the reaction mixture added to the catalyst had a pH of 9.3. In this case, the pH was adjusted by adding LiOH.

The lifetime achieved in this experiment was approx. 32 days.

EXAMPLE 2

Example 1 was essentially repeated, except that the pH was adjusted by using KOH. The lifetime achieved in this experiment was approx. 25 days.

COMPARATIVE EXAMPLE 3

In a trickle bed reactor, a mixture of acetone-cyanohydrin, water and acetone was reacted at a temperature of 50° C. and at standard pressure with a commercially available $MnO_2$ catalyst which had been compressed to a granule, had a BET surface area of approx. 230 $m^2/g$ and a structure number 44-0141 according to ICDD, and whose X-ray spectrum (XRD) exhibited a reflection with maximum intensity in the range of 32° to 42°. The mixing ratio of the acetone cyanohydrin/acetone/water components was 1/1.5/6. The loading of the catalyst was approx. 1.55 to 1.60 g of acetone cyanohydrin per g of catalyst per hour.

The reaction mixture added to the catalyst had a pH of approx. 4.1. In addition, approx. 300 ml of air per minute at a pressure of approx. 1 bar were used, and the amount of catalyst was approx. 50 g. The lifetime achieved in this experiment was approx. 26 days.

EXAMPLE 3

Comparative Example 3 was essentially repeated, except that the reaction mixture added to the catalyst had a pH of 9.3. In this case, the pH was adjusted by adding LiOH.

The lifetime achieved in this experiment was approx. 58 days.

COMPARATIVE EXAMPLE 4

Comparative Example 2 was essentially repeated, except that the pH was adjusted with diethylamine. The lifetime was approx. 5 days. This comparative example shows that the use of amines can lead to disadvantageous effects.

The invention claimed is:

1. A process for preparing a carboxamide, the process comprising:
    reacting a carbonitrile and water in the presence of i) a catalyst comprising manganese dioxide, ii) an oxidizing agent, and iii) lithium ions, thereby hydrolyzing the carbonitrile to obtain a carboxamide,
    wherein the carbonitrile, the water, and the lithium ions are present in a reaction mixture, which is added to the catalyst and has a pH in a range from 6.0 to 11.0.

2. The process of claim 1, wherein the oxidizing agent is a gas comprising oxygen.

3. The process of claim 2, wherein the gas comprises molecular oxygen ($O_2$) or ozone ($O_3$).

4. The process of claim 2, wherein the gas comprises, by volume:
    50 to 98% of an inert gas; and
    2 to 50% of molecular oxygen ($O_2$).

5. The process of claim 2, wherein a concentration of the gas comprising oxygen is in the range of 10 to 1000 liters/hour, based on 1 kg of the catalyst.

6. The process of claim 1, wherein the reaction mixture has a pH in a range from 6.5 to 10.0.

7. The process of claim 1, wherein the pH of the reaction mixture is adjusted by adding lithium oxide.

8. The process of claim 1, wherein the pH of the reaction mixture is not adjusted with an amine.

9. The process of claim 1, wherein the reaction mixture further comprises an amine and a concentration of the amine in the reaction mixture is at most 0.001% by weight.

10. The process of claim 1, wherein the pH of the reaction mixture is adjusted by adding lithium hydroxide.

11. The process of claim 1, wherein the catalyst comprises at least 50% by weight of manganese dioxide having a formula of $MnO_x$ wherein x is in a range of 1.7 to 2.0.

12. The process of claim 1, wherein the catalyst further comprises at least one promoter selected from the group consisting of Ti, Zr, V, Nb, Ta, Cr, Mo, W, Zn, Ga, In, Ge, Sn, and Pt.

13. The process of claim 12, wherein a content of the promoter in the catalyst is in a range from 0.01 to 10% by weight.

14. The process of claim 1, wherein the catalyst has a specific surface area in a range from 50 to 1000 $m^2$ per g.

15. The process of claim 1, wherein the carbonitrile is an α-hydroxycarbonitrile.

16. The process of claim 15, wherein the α-hydroxycarbonitrile is 2-hydroxy-2-methylpropionitrile or 2-hydroxypropionitrile.

17. The process of claim 1, wherein the reaction mixture further comprises at least one solvent selected from the group consisting of acetone, acetaldehyde, propanal, and butanal.

18. The process of claim 17, wherein a concentration of the aldehyde or ketone compound in the reaction mixture is in a range from 0.1 to 6 mol per mole of carbonitrile.

19. The process of claim 1, wherein a molar ratio of water to carbonitrile in the reaction mixture is in a range from 0.5:1-25:1.

20. The process of claim 1, wherein the reacting is carried out at a temperature in a range from 10 to 150° C.

21. The process of claim 1, wherein the reacting is carried out at a pressure in a range from 0.1 bar to 10 bar.

22. The process of claim 1, wherein the reacting is carried out in a trickle bed reactor.

23. The process of claim 1, wherein the catalyst has, in the X-ray spectrum (XRD) measured as a powder, a reflection in a range from 32.0 to 42.0°.

24. The process of claim 1, wherein the catalyst comprises, by weight percent, based on a total weight of the catalyst:
   0.0 to 25% of $SiO_2$;
   0.1 to 10% of $K_2O$; and
   0.0 to 5% of $ZrO_2$
   75 to 99% of $MnO_2$.

25. The process of claim 1, wherein the reaction mixture has a pH in a range from 8.5 to 11.0.

26. The process of claim 1, wherein the reaction mixture has a pH in a range from 8.5 to 10.0.

27. The process of claim 1, wherein the reaction mixture has a pH in a range from 8.5 to 9.5.

* * * * *

UNITED STATES PATENT AND TRADEMARK OFFICE
CERTIFICATE OF CORRECTION

| | | |
|---|---|---|
| PATENT NO. | : 8,334,406 B2 | Page 1 of 1 |
| APPLICATION NO. | : 12/515036 | |
| DATED | : December 18, 2012 | |
| INVENTOR(S) | : Alexander May et al. | |

It is certified that error appears in the above-identified patent and that said Letters Patent is hereby corrected as shown below:

On the title page, Item (54) and column 1, the title is incorrect. Item (54) and column 1 should read:

-- (54) PROCESS FOR PREPARING CARBOXAMIDES BY HYDROLYSIS OF CARBOXYLIC ACID NITRILES IN THE PRESENCE OF A CATALYST COMPRISING MANGANESE DIOXIDE --

Signed and Sealed this
Twenty-sixth Day of March, 2013

Teresa Stanek Rea
*Acting Director of the United States Patent and Trademark Office*